United States Patent
Moribe et al.

(10) Patent No.: US 6,426,996 B1
(45) Date of Patent: Jul. 30, 2002

(54) X-RAY RADIOGRAPHIC/FLUOROSCOPIC APPARATUS, X-RAY RADIOGRAPHIC METHOD AND X-RAY RADIOGRAPHIC/FLUOROSCOPIC METHOD

(75) Inventors: Yoshio Moribe; Akira Izuhara, both of Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/686,226

(22) Filed: Oct. 11, 2000

(30) Foreign Application Priority Data

Nov. 8, 1999 (JP) .......................................... 11-316582

(51) Int. Cl.[7] .............................................. A61B 6/302
(52) U.S. Cl. ....................................... 378/116; 378/138
(58) Field of Search ................................. 378/114, 115, 378/116, 119, 134, 136, 138, 98.2, 108

(56) References Cited

U.S. PATENT DOCUMENTS

| | | | |
|---|---|---|---|
| 4,685,118 A | * | 8/1987 | Furbee et al. ............... 378/114 |
| 5,878,107 A | * | 3/1999 | Ishikawa et al. ........... 378/98.2 |
| 6,075,837 A | * | 6/2000 | Roos et al. ................. 378/98.2 |
| 6,222,907 B1 | * | 4/2001 | Gordon, III et al. ........ 378/116 |

* cited by examiner

Primary Examiner—David P. Porta
(74) Attorney, Agent, or Firm—Moonray Kojima

(57) ABSTRACT

In order to produce X-ray radiographic images consistently with high quality regardless of the magnitude of body thickness or motion of an examined site, a radiographic irradiation time threshold readout section 4 reads a radiographic irradiation time threshold Th corresponding to an examined site input by an operator out of a radiographic irradiation time threshold table 3, and an irradiation condition determining section 5 and radiographic irradiation time comparing section 6 select a larger radiographic focus size as the radiographic focus size for an X-ray tube 1 if Th<radiographic irradiation time Ts, and select a smaller radiographic focus size if Th radiographic irradiation time Ts.

15 Claims, 7 Drawing Sheets

FIG. 1 [PRIOR ART]
X-ray radiographic/fluoroscopic apparatus
500
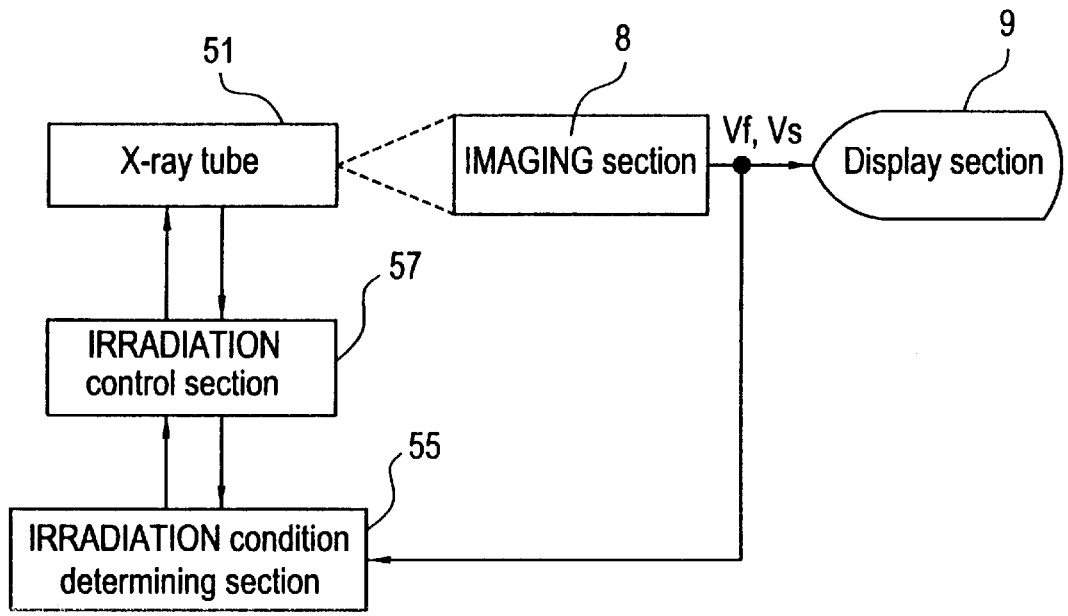
FIG. 2 [PRIOR ART]
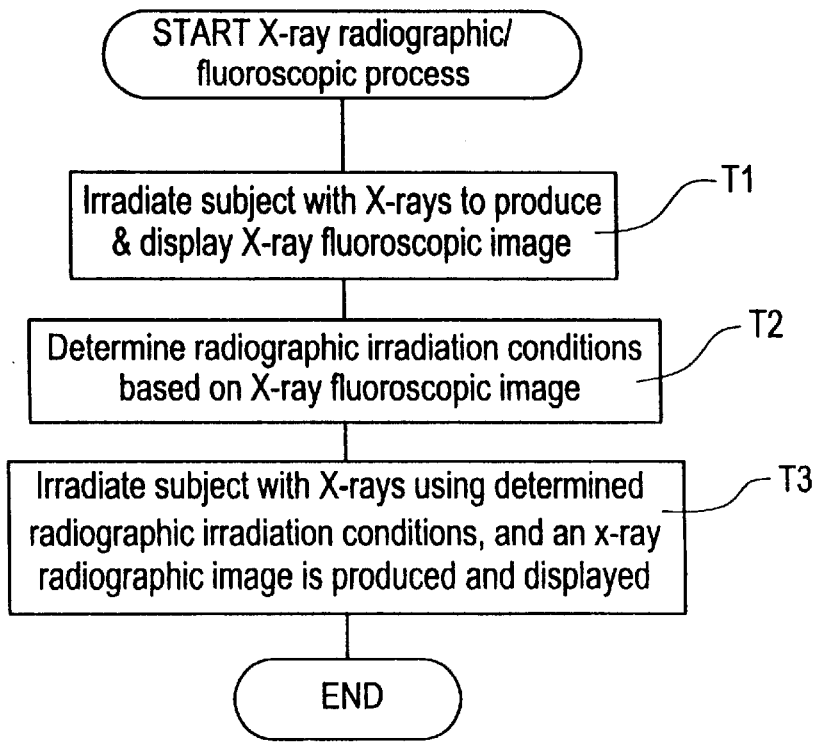

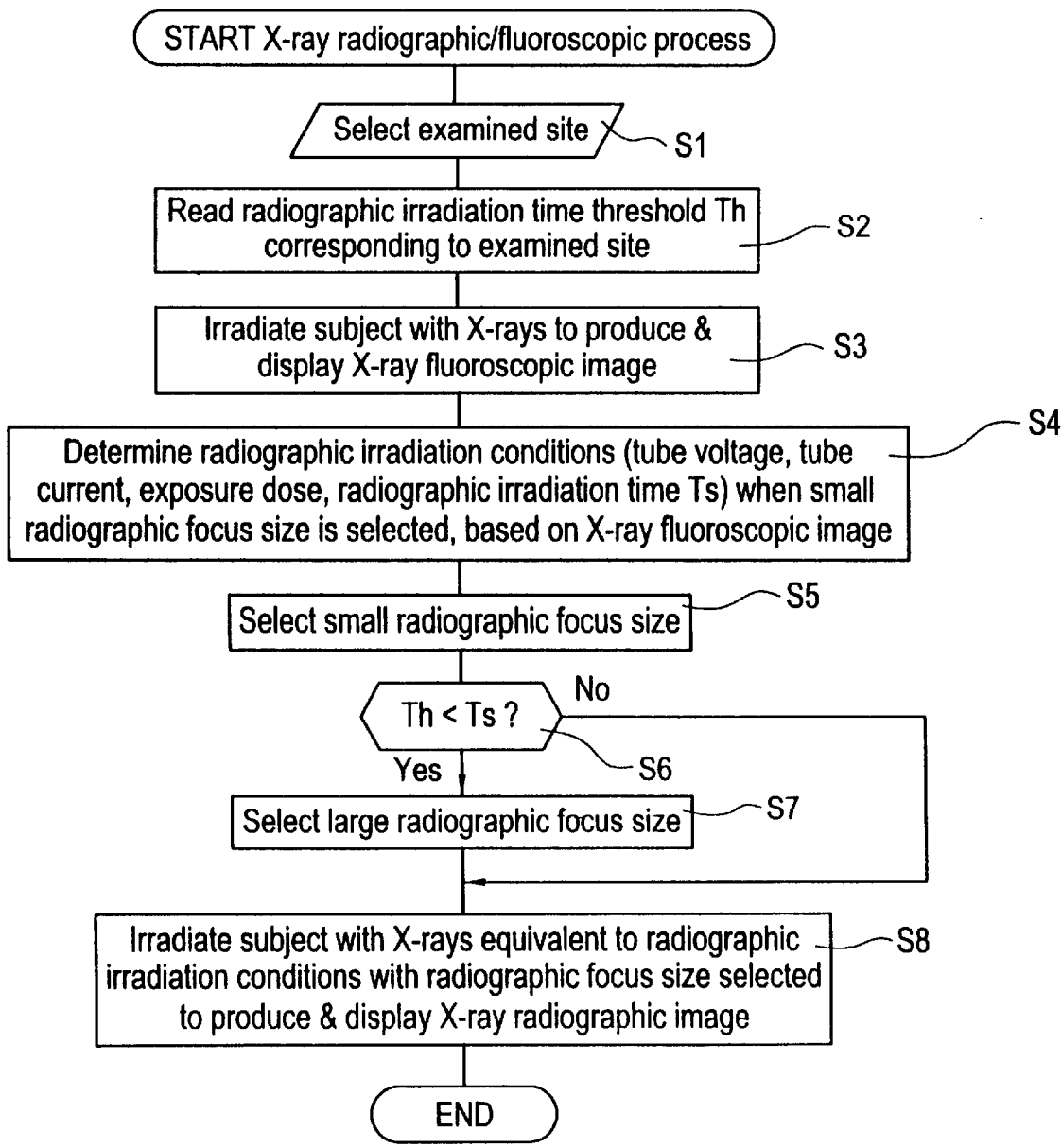

X-RAY RADIOGRAPHIC/FLUOROSCOPIC APPARATUS, X-RAY RADIOGRAPHIC METHOD AND X-RAY RADIOGRAPHIC/ FLUOROSCOPIC METHOD

BACKGROUND OF THE INVENTION

The present invention relates to an X-ray radiographic/ fluoroscopic apparatus, X-ray radiographic method and X-ray radiographic/fluoroscopic method, and more particularly to an X-ray radiographic/fluoroscopic apparatus, X-ray radiographic method and X-ray radiographic/fluoroscopic method that can consistently produce X-ray radiographic images with high quality regardless of the magnitude of body thickness or motion of an examined site.

FIG. 1 illustrates the configuration of an example of a conventional X-ray radiographic/fluoroscopic apparatus.

The X-ray radiographic/fluoroscopic apparatus 500 comprises an X-ray tube 51 in which a single fluoroscopic focus size or a single radiographic focus size is set, an irradiation condition determining section 55 for determining fluoroscopic irradiation conditions and radiographic irradiation conditions (such as the tube voltage and tube current of the X-ray tube 51, exposure dose and radiographic irradiation time), an irradiation control section 57 for controlling the operation of the X-ray tube 51, an imaging section 8 comprising an image intensifier or TV camera or the like for capturing an X-ray fluoroscopic image or X-ray radiographic image of a subject and outputting a fluoroscopic video signal Vf or radiographic video signal Vs, and a display section 9 for displaying an X-ray fluoroscopic image or X-ray radiographic image based on the fluoroscopic video signal Vf or radiographic video signal Vs.

FIG. 2 is a flow chart illustrating an X-ray radiographic/ fluoroscopic process by the X-ray radiographic/fluoroscopic apparatus 500.

In Step T1, a subject is irradiated with X-rays based on predefined fluoroscopic irradiation conditions, and an X-ray fluoroscopic image is produced and displayed. The fluoroscopic focus size is 0.3 mm, for example, and the input power rating of the X-ray tube 51 in this case is on the order of 10 kW (or less), for example.

In Step T2, body thickness is calculated based on the X-ray fluoroscopic image to determine radiographic irradiation conditions from the body thickness. The radiographic focus size is 0.6 mm, for example, and the input power rating of the X-ray tube 51 in this case is on the order of 30–40 kW, for example.

In Step T3, the subject is irradiated with X-rays using the determined radiographic irradiation conditions, and an X-ray radiographic image is produced and displayed.

Generally, when the X-rays are emitted from the X-ray tube 51 with a large focus size, an umbra and penumbra of the X-rays tend to simultaneously appear on the image plane, and the image resolution is liable to be degraded. Therefore, the focus size is preferably made small for improved resolution.

On the other hand, when the focus size is small, the input power rating of the X-ray tube 51 is reduced, and hence the radiographic irradiation time (imaging time) required for the same exposure dose is prolonged, leading to a problem that the image is subject to blurring in radiographing an examined site having a large body thickness or large motion. Especially when the gastric wall is radiographed with a contrast material such as barium applied, blurring gets worse due to vibration of the X-ray tube 51 or the gastric wall and rundown of the barium from the gastric wall etc.

SUMMARY OF THE INVENTION

It is an object of the present invention to provide an X-ray radiographic/fluoroscopic apparatus, X-ray radiographic method and X-ray radiographic/fluoroscopic method that can consistently produce X-ray radiographic images with high quality regardless of the magnitude of the body thickness or motion of an examined site.

In accordance with a first aspect of the present invention, there is provided an X-ray radiographic/fluoroscopic apparatus comprising: X-ray emitting means having a function of emitting X-rays with a focus selected from at least one fluoroscopic focus size and a plurality of radiographic focus sizes; X-ray fluoroscopic image producing means for producing an X-ray fluoroscopic image by irradiating a subject with X-rays with the fluoroscopic focus size selected; radiographic focus size selecting means for selecting a relatively large radiographic focus size in radiographing an examined site having a relatively large body thickness, and selecting a relatively small radiographic focus size in radiographing an examined site having a relatively small body thickness; and X-ray radiographic image producing means for producing an X-ray radiographic image by irradiating the subject with X-rays equivalent to radiographic irradiation conditions determined based on the X-ray fluoroscopic image with the selected radiographic focus size.

In accordance with a second aspect of the present invention, there is provided an X-ray radiographic/ fluoroscopic apparatus comprising: X-ray emitting means having a function of emitting X-rays with a focus selected from at least one fluoroscopic focus size and a plurality of radiographic focus sizes; X-ray fluoroscopic image producing means for producing an X-ray fluoroscopic image by irradiating a subject with X-rays with said fluoroscopic focus size selected; radiographic focus size selecting means for selecting a relatively large radiographic focus size in radiographing an examined site having a relatively large motion, and selecting a relatively small radiographic focus size in radiographing an examined site having a relatively small motion; and X-ray radiographic image producing means for producing an X-ray radiographic image by irradiating the subject with X-rays equivalent to radiographic irradiation conditions determined based on said X-ray fluoroscopic image with said selected radiographic focus size.

In accordance with a third aspect of the present invention, there is provided an X-ray radiographic/fluoroscopic apparatus comprising: X-ray emitting means having a function of emitting X-rays with a focus selected from at least one fluoroscopic focus size and a plurality of radiographic focus sizes; examined site input means for receiving an examined site from an operator; radiographic irradiation time threshold defining means for defining a radiographic irradiation time threshold that is an upper limit of a radiographic irradiation time corresponding to said examined site; X-ray fluoroscopic image producing means for producing an X-ray fluoroscopic image by irradiating a subject with X-rays with said fluoroscopic focus size selected; radiographic focus size selecting means for selecting a relatively large radiographic focus size if a radiographic irradiation time determined based on said X-ray fluoroscopic image is longer than said radiographic irradiation time threshold, and selecting a relatively small radiographic focus size if said determined radiographic irradiation time is shorter than said radiographic irradiation time threshold; and X-ray radiographic image producing means for producing an X-ray radiographic image by irradiating the subject with X-rays with said selected radiographic focus size.

In accordance with a fourth aspect of the present invention, there is provided an X-ray radiographic/fluoroscopic apparatus comprising: X-ray emitting means having a function of emitting X-rays with a focus selected from at least one fluoroscopic focus size and a plurality of radiographic focus sizes; X-ray fluoroscopic image producing means for producing an X-ray fluoroscopic image by irradiating a subject with X-rays with said fluoroscopic focus size selected; radiographic irradiation time threshold input means for receiving from an operator a radiographic irradiation time threshold that is an upper limit of a radiographic irradiation time corresponding to an examined site; radiographic focus size selecting means for selecting a relatively large radiographic focus size if a radiographic irradiation time determined based on said X-ray fluoroscopic image is longer than said radiographic irradiation time threshold, and selecting a relatively small radiographic focus size if said determined radiographic irradiation time is shorter than said radiographic irradiation time threshold; and X-ray radiographic image producing means for producing an X-ray radiographic image by irradiating the subject with X-rays equivalent to radiographic irradiation conditions determined based on said X-ray fluoroscopic image with said selected radiographic focus size.

In accordance with a fifth aspect of the present invention, there is provided an X-ray radiographic/fluoroscopic apparatus comprising: X-ray emitting means having a function of emitting X-rays with a focus selected from at least one fluoroscopic focus size and a plurality of radiographic focus sizes; examined site input means for receiving an examined site from an operator; X-ray fluoroscopic image producing means for producing an X-ray fluoroscopic image by irradiating a subject with X-rays with said fluoroscopic focus size selected; radiographic irradiation condition determining means for determining radiographic irradiation conditions based on said X-ray fluoroscopic image; radiographic focus size selecting means for selecting a radiographic focus size for use in X-ray radiography based on said examined site and said radiographic irradiation conditions; and X-ray radiographic image producing means for producing an X-ray radiographic image by irradiating the subject with X-rays equivalent to said radiographic irradiation conditions with said selected radiographic focus size.

In accordance with a sixth aspect of the invention, there is provided the X-ray radiographic/fluoroscopic apparatus of the above configuration, wherein the X-ray emitting means has a plurality of fluoroscopic focus sizes.

In accordance with a seventh aspect of the invention, there is provided the X-ray radiographic/fluoroscopic apparatus as defined by any one of the claims wherein said X-ray emitting means has three or more radiographic focus sizes.

In accordance with a eighth aspect of the present invention, there is provided an X-ray radiographic method comprising the step of producing an X-ray radiographic image by irradiating a subject with X-rays with a relatively large radiographic focus size in radiographing an examined site having a relatively large body thickness, and by irradiating the subject with X-rays with a relatively small radiographic focus size in radiographing an examined site having a relatively small body thickness.

In accordance with a ninth aspect of the present invention, there is provided an X-ray radiographic method comprising the step of producing an X-ray radiographic image by irradiating a subject with X-rays with a relatively large radiographic focus size in radiographing an examined site having a relatively large motion, and by irradiating the subject with X-rays with a relatively small radiographic focus size in radiographing an examined site having a relatively small motion.

In accordance with a tenth aspect of the invention, there is provided the X-ray radiographic method of the above configuration, wherein the radiographic focus size for use in radiography is selected from among three or more radiographic focus sizes.

In accordance with a eleventh aspect of the present invention, there is provided an X-ray radiographic/fluoroscopic method comprising the steps of: producing an X-ray fluoroscopic image by irradiating a subject with X-rays with a fluoroscopic focus size; selecting a relatively large radiographic focus size from among a plurality of radiographic focus sizes in radiographing an examined site having a relatively large body thickness, and selecting a relatively small radiographic focus size in radiographing an examined site having a relatively small body thickness; and producing an X-ray radiographic image by irradiating the subject with X-rays equivalent to radiographic irradiation conditions determined based on said X-ray fluoroscopic image with said selected radiographic focus size.

In accordance with a twelfth aspect of the present invention, there is provided an X-ray radiographic/fluoroscopic method comprising the steps of: producing an X-ray fluoroscopic image by irradiating a subject with X-rays with a fluoroscopic focus size; selecting a relatively large radiographic focus size from among a plurality of radiographic focus sizes in radiographing an examined site having a relatively large motion, and selecting a relatively small radiographic focus size in radiographing an examined site having a relatively small motion; and producing an X-ray radiographic image by irradiating the subject with X-rays equivalent to radiographic irradiation conditions determined based on said X-ray fluoroscopic image with said selected radiographic focus size.

In accordance with a thirteenth aspect of the present invention, there is provided an X-ray radiographic/fluoroscopic method comprising the steps of: producing an X-ray fluoroscopic image by irradiating a subject with X-rays with a fluoroscopic focus size; receiving an examined site from an operator to define a radiographic irradiation time threshold that is an upper limit of a radiographic irradiation time corresponding to said examined site; selecting a relatively large radiographic focus size from among a plurality of radiographic focus sizes if a radiographic irradiation time determined based on said X-ray fluoroscopic image is longer than said radiographic irradiation time threshold, and selecting a relatively small radiographic focus size if said determined radiographic irradiation time is shorter than said radiographic irradiation time threshold; and producing an X-ray radiographic image by irradiating the subject with X-rays equivalent to radiographic irradiation conditions determined based on said X-ray fluoroscopic image with said selected radiographic focus size.

In accordance with a fourteenth aspect of the present invention, there is provided an X-ray radiographic/fluoroscopic method comprising the steps of: producing an X-ray fluoroscopic image by irradiating a subject with X-rays with a fluoroscopic focus size; receiving from an operator a radiographic irradiation time threshold that is an upper limit of a radiographic irradiation time corresponding to an examined site; selecting a relatively large radiographic focus size from among a plurality of radiographic focus sizes if a radiographic irradiation time determined based on said X-ray fluoroscopic image is longer than said radiographic irradiation time threshold, and selecting a relatively small radiographic focus size if said determined radiographic irradiation time is shorter than said radiographic irradiation time threshold; and producing an X-ray radiographic image by irradiating the subject with X-rays equivalent to radiographic irradiation conditions determined based on said X-ray fluoroscopic image with said selected radiographic focus size.

In accordance with a fifteenth aspect of the present invention, there is provided an X-ray radiographic/fluoroscopic method comprising the steps of: producing an X-ray fluoroscopic image by irradiating a subject with X-rays with a fluoroscopic focus size; determining radiographic irradiation conditions based on said X-ray fluoroscopic image; selecting a radiographic focus size for use in X-ray radiography from among a plurality of radiographic focus sizes based on an examined site and said radiographic irradiation conditions; and producing an X-ray radiographic image by irradiating the subject with X-rays equivalent to said radiographic irradiation conditions with said selected radiographic focus size.

In accordance with a sixteenth aspect of the invention, there is provided the X-ray radiographic/fluoroscopic method of the above configuration, wherein the radiographic focus size for use in radiography is selected from among three or more radiographic focus sizes.

According to the X-ray radiographic/fluoroscopic apparatus of the first aspect, X-ray radiographic method of the eighth aspect and X-ray radiographic/fluoroscopic method of the eleventh aspect, when an examined site having a relatively large body thickness is radiographed, the radiography is performed with a relatively large radiographic focus size selected, whereby the X-ray irradiation strength is enhanced and the radiographic irradiation time reduced to reduce blurring of the examined site. When an examined site having a relatively small body thickness is radiographed, the radiography is performed with a relatively small radiographic focus size selected, whereby the resolution of the X-ray radiographic image is improved.

Consequently, X-ray radiographic images can be consistently produced with high quality regardless of the body thickness.

According to the X-ray radiographic/fluoroscopic apparatus of the second aspect, X-ray radiographic method of the ninth aspect and X-ray radiographic/fluoroscopic method of the twelfth aspect, when an examined site having a relatively large motion is radiographed, the radiography is performed with a relatively large radiographic focus size selected, whereby the X-ray irradiation strength is enhanced and the radiographic irradiation time reduced to reduce blurring of the examined site. When an examined site having a relatively small motion is radiographed, the radiography is performed with a relatively small radiographic focus size selected, whereby the resolution of the X-ray radiographic image is improved.

Consequently, X-ray radiographic images can be consistently produced with high quality regardless of the magnitude of motion of the examined site.

According to the X-ray radiographic/fluoroscopic apparatus of the third aspect and X-ray radiographic/fluoroscopic method of the thirteenth aspect, since a shorter radiographic irradiation time threshold is defined for an examined site having a larger degree of body thickness or motion, when an examined site having a relatively large body thickness or motion is radiographed, a relatively large radiographic focus size is selected and blurring of the examined site can be reduced. When an examined site having a relatively small body thickness or motion is radiographed, a relatively small radiographic focus size is selected and an X-ray radiographic image can be produced with high resolution.

According to the X-ray radiographic/fluoroscopic apparatus of the fourth aspect and X-ray radiographic/fluoroscopic method of the fourteenth aspect, the operator can finely specify a radiographic irradiation time threshold in conformity with image quality preferences or clinical interest while viewing an X-ray fluoroscopic image.

According to the X-ray radiographic/fluoroscopic apparatus of the fifth aspect and X-ray radiographic/fluoroscopic method of the fifteenth aspect, since the radiographic focus size for use in X-ray radiography is selected based on an examined site and radiographic irradiation conditions, X-ray radiographic images can be consistently produced with high quality regardless of the magnitude of body thickness or motion of the examined site.

According to the X-ray radiographic/fluoroscopic apparatus of the sixth aspect, since the fluoroscopic focus size for use in fluoroscopy can be selected from among a plurality of fluoroscopic focus sizes, image quality of the X-ray fluoroscopic image can be improved.

According to the X-ray radiographic/fluoroscopic apparatus of the seventh aspect, X-ray radiographic method of the tenth aspect and X-ray radiographic/fluoroscopic method of the sixteenth aspect, since the radiographic focus size for use in radiography can be selected from among three or more radiographic focus sizes, a radiographic focus size suitable for radiography of the examined site can be more finely selected.

Thus, according to the X-ray radiographic/fluoroscopic apparatus, X-ray radiographic method and X-ray radiographic/fluoroscopic method of the present invention, since the radiographic focus size is changed with the magnitude of body thickness or motion of the examined site, an advantage resulting from magnification of the radiographic focus size (i.e., reduction of blurring by reducing the irradiation time) and an advantage resulting from reduction of the radiographic focus size (i.e., improvement of resolution by suppressing penumbra formation) can be simultaneously obtained in a good proportion, and X-ray radiographic images can be stably obtained with high quality.

Further objects and advantages of the present invention will be apparent from the following description of the preferred embodiments of the invention as illustrated in the accompanying drawings.

BRIEF DESCRIPTION OF THE DRAWINGS

FIG. 1 illustrates the configuration of an example of a conventional X-ray radiographic/fluoroscopic apparatus.

FIG. 2 is a flow chart illustrating an X-ray radiographic/fluoroscopic process by the X-ray radiographic/fluoroscopic apparatus shown in FIG. 1.

FIG. 4 illustrates the content of the radiographic irradiation time threshold table in the X-ray radiographic/fluoroscopic apparatus of FIG. 3.

FIG. 5 is a flow chart illustrating an X-ray radiographic/fluoroscopic process by the X-ray radiographic/fluoroscopic apparatus of FIG. 3.

DETAILED DESCRIPTION OF THE INVENTION

The present invention will now be described in more detail with reference to embodiments shown in the accompanying drawings.

First Embodiment

Figure 3:
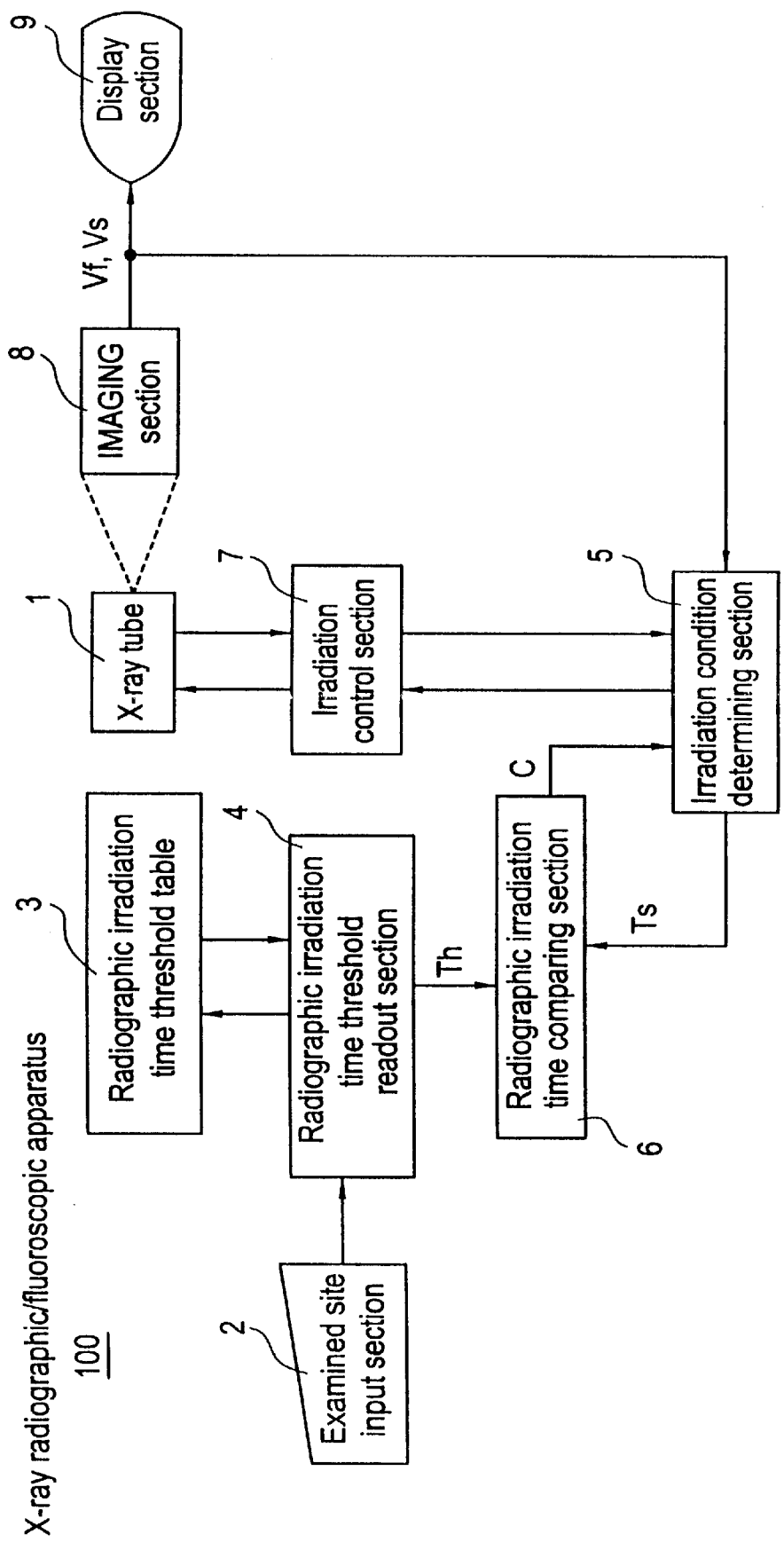
FIG. 3 illustrates the configuration of an X-ray radiographic/fluoroscopic apparatus in accordance with a first embodiment of the present invention.

FIG. 3 illustrates the configuration of an X-ray radiographic/fluoroscopic apparatus in accordance with a first embodiment of the present invention.

The X-ray radiographic/fluoroscopic apparatus 100 comprises an X-ray tube 1 having a function of emitting X-rays with a focus selected from a single fluoroscopic focus size and a plurality of radiographic focus sizes, an examined site input section 2 for receiving an examined site from a human operator (physician or technician), a radiographic irradiation time threshold table 3 for previously storing an upper limit of the radiographic irradiation time corresponding to each examined site, i.e., a radiographic irradiation time threshold Th, a radiographic irradiation time threshold readout section 4 for reading the radiographic irradiation time threshold Th corresponding to the examined site received from the operator out of the radiographic irradiation time threshold table 3, an irradiation condition determining section 5 for determining fluoroscopic irradiation conditions and radiographic irradiation conditions (such as the tube voltage, tube current, exposure dose, and radiographic irradiation time Ts), a radiographic irradiation time comparing section 6 for comparing the readout radiographic irradiation time threshold Th and the radiographic irradiation time Ts and sending the result C of the comparison to the irradiation condition determining section 5, an irradiation control section 7 for controlling the operation of the X-ray tube 1 in accordance with the fluoroscopic irradiation conditions or radiographic irradiation conditions determined in the irradiation condition determining section 5, an imaging section 8 comprising an image intensifier or TV camera or the like, for capturing an X-ray fluoroscopic image or an X-ray radiographic image of a subject (which is generally a medical patient) and outputting a fluoroscopic video signal Vf or a radiographic video signal Vs, and a display section 9 for displaying the X-ray fluoroscopic image or X-ray radiographic image based on the fluoroscopic video signal Vf or radiographic video signal Vs.

The fluoroscopic focus size is 0.3 mm, for example, and the input power rating of the X-ray tube 1 in this case is on the order of 10 kW (or less), for example.

The radiographic focus size is, for example, selected from between 0.6 mm and 1.25 mm. If the former is selected, the input power rating of the X-ray tube 1 is 34 kW, the tube voltage rating is 70 kV, and the tube current rating is 140 mA, for example. If the latter is selected, the input power rating is 76 kW, the tube voltage rating is 70 kV, and the tube current rating is 560 mA, for example.

FIG. 4 illustrates the content of the radiographic irradiation time threshold table 3.

A radiographic irradiation time threshold Th is stored for each examined site.

A relatively short radiographic irradiation time threshold Th is stored for an examined site in which a combined value of the degree of (standard) body thickness and vibration is large, and a relatively long radiographic irradiation time threshold Th is stored for an examined site in which the combined value is small. For example, the radiographic irradiation time threshold Th is 5 ms for the "Stomach", which has a relatively large combined value, and the radiographic irradiation time threshold Th is 10 ms for the "Small & large intestines", which have a relatively small combined value. Note that the vibration speed of the "Stomach" is on the order of 28 mm/sec, for example.

FIG. 5 is a flow chart illustrating an X-ray radiographic/fluoroscopic process by the X-ray radiographic/fluoroscopic apparatus 100.

In Step S1, the operator inputs an examined site using the examined site input section 2.

In Step S2, a radiographic irradiation time threshold Th corresponding to the examined site is read out of the radiographic irradiation time threshold table 3. In the example shown in FIG. 4, if the examined site is the "Stomach", for example, Th=5 ms is read out.

In Step S3, the subject is irradiated with X-rays based on predefined fluoroscopic irradiation conditions, and an X-ray fluoroscopic image is produced and displayed.

In Step S4, the body thickness is calculated based on the X-ray fluoroscopic image to determine radiographic irradiation conditions (which can properly set image brightness on the image plane) when the X-rays are emitted with a small radiographic focus size selected. Alternatively, the operator may manually specify the radiographic irradiation conditions while viewing the X-ray fluoroscopic image. The radiographic irradiation conditions are, for example, an exposure dose of 0.14 mAs and a radiographic irradiation time Ts of 10 ms.

In Step S5, a small radiographic focus size is selected. In the above example, a radiographic focus size of 0.6 mm is selected.

In Step S6, the radiographic irradiation time threshold Th read at Step S2 and the radiographic irradiation time Ts determined at Step S4 are compared, and if Th<Ts, the process goes to Step S7; otherwise (i.e., if Th≧Ts) to Step S8. In the example above, Th=5 ms and Ts=10 ms, and the process therefore goes to Step S7.

In Step S7, a larger radiographic focus size is selected. In the example above, a radiographic focus size of 1.25 mm is selected.

In Step S8, the subject is irradiated with X-rays equivalent to the radiographic irradiation conditions (i.e., X-rays of identical exposure dose) with the radiographic focus size selected at Step S5 or S7, and an X-ray radiographic image is produced and displayed. In the example above, since the large radiographic focus size (which has a tube current rating four times that of the small radiographic focus size) is selected, X-rays equivalent to the radiographic irradiation conditions may be emitted within a radiographic irradiation time on the order of Ts/4.

Figure 6:
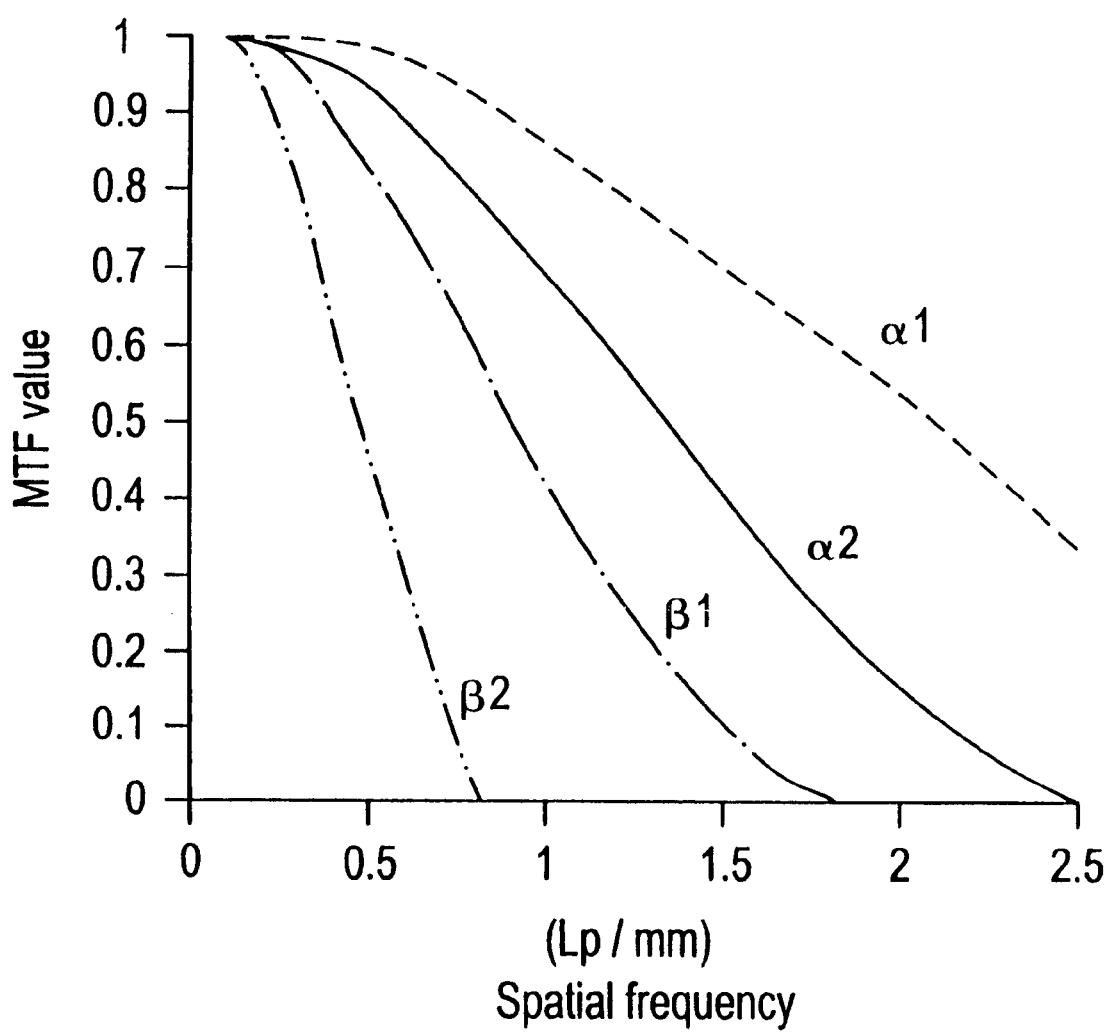
FIG. 6 is a characteristic diagram illustrating the result of simulation of spatial frequency—MTF value characteristics.

FIG. 6 is a characteristic diagram illustrating the result of simulation of spatial frequency—MTF (modulation transfer function) value characteristics when two examined sites having constant vibration and different body thicknesses are irradiated with X-rays with large and small radiographic focus sizes.

The characteristic curve α1 indicated by a dotted line is obtained on the assumption that an examined site having a small body thickness on the order of 20 cm, for example, is radiographed with a small radiographic focus size (0.6 mm).

The characteristic curve α2 indicated by a solid line is obtained on the assumption that an examined site having a small body thickness is radiographed with a large radiographic focus size (1.25 mm). The resolution is better for the characteristic curve α1, which has a higher spatial frequency with respect to the same MTF value. That is, when an examined site having a small body thickness is to be radiographed, it is preferred that a small radiographic focus size be selected.

The characteristic curve β1 indicated by a dot-dash line is obtained on the assumption that an examined site having a large body thickness on the order of 30 cm, for example, is radiographed with a large radiographic focus size. The characteristic curve β2 indicated by a double-dot-dash line is obtained when a subject having a large body thickness is radiographed with a small radiographic focus size. The resolution is better for the characteristic curve β1, which has a higher spatial frequency with respect to the same MTF value. That is, when an examined site having a large body thickness is to be radiographed, it is preferred that a large radiographic focus size be selected.

Although no characteristics are illustrated, when examined sites having a constant body thickness and having large and small motions are assumed to be irradiated with X-rays with large and small radiographic focus sizes, the resolution can be improved by selecting the large radiographic focus size for the examined site having a large motion to reduce the radiographic irradiation time; and the resolution can be improved by selecting the small radiographic focus size for the examined site having a small motion to suppress penumbra formation.

According to the X-ray radiographic/fluoroscopic apparatus 100, a shorter radiographic irradiation time threshold Th is predefined when the combined value of the degree of body thickness and motion is large. If the radiographic irradiation time Ts is longer than the radiographic irradiation time threshold Th, a larger radiographic focus size is selected, and thus the radiographic irradiation time can be reduced and blurring of the examined site can be mitigated. If the radiographic irradiation time Ts is shorter than the radiographic irradiation time threshold Th, a small radiographic focus size is selected, and thus penumbra formation can be suppressed and resolution of the X-ray radiographic image can be improved.

Second Embodiment

Figure 7:
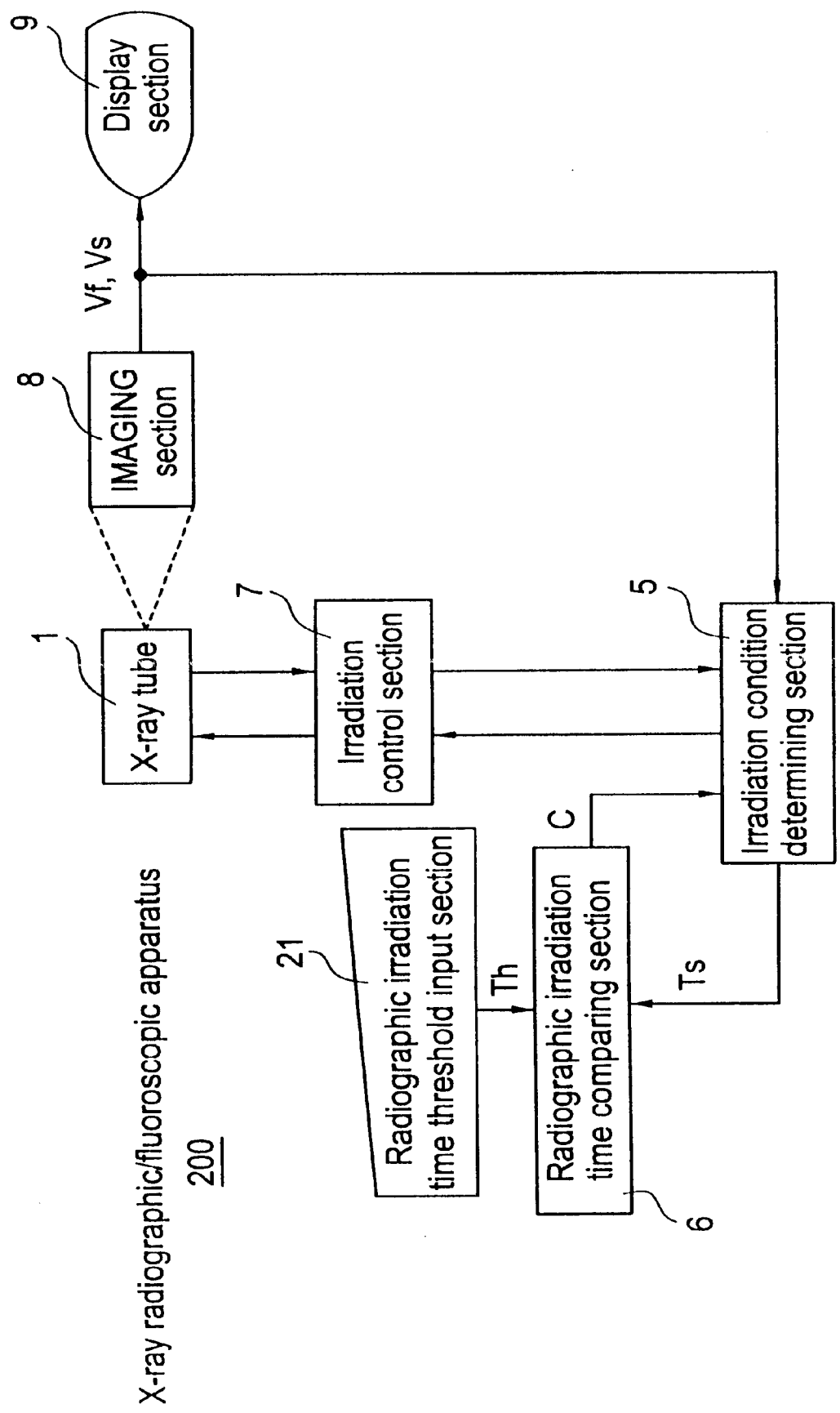
FIG. 7 illustrates the configuration of an X-ray radiographic/fluoroscopic apparatus in accordance with a second embodiment of the present invention.

FIG. 7 illustrates the configuration of an X-ray radiographic/fluoroscopic apparatus in accordance with a second embodiment of the present invention.

The X-ray radiographic/fluoroscopic apparatus 200 comprises a radiographic irradiation time threshold input section 21 for receiving a radiographic irradiation time threshold Th from the operator, an irradiation condition determining section 5 for determining fluoroscopic irradiation conditions and radiographic irradiation conditions (such as the tube voltage, tube current, exposure dose and radiographic irradiation time Ts), and a radiographic irradiation time comparing section 6 for comparing the radiographic irradiation time threshold Th and the radiographic irradiation time Ts and sending the result C of the comparison to the irradiation condition determining section 5. The X-ray tube 1, irradiation control section 7, imaging section 8 and display section 9 are the same components as those of the X-ray radiographic/fluoroscopic apparatus 100 of the first embodiment.

According to the X-ray radiographic/fluoroscopic apparatus 200, since the radiographic irradiation time threshold Th is input by the operator, the configuration can be simplified. Moreover, the operator can finely specify the radiographic irradiation time threshold Th in conformity with image quality preferences or clinical interest while viewing an X-ray fluoroscopic image.

Third Embodiment

Figure 8:
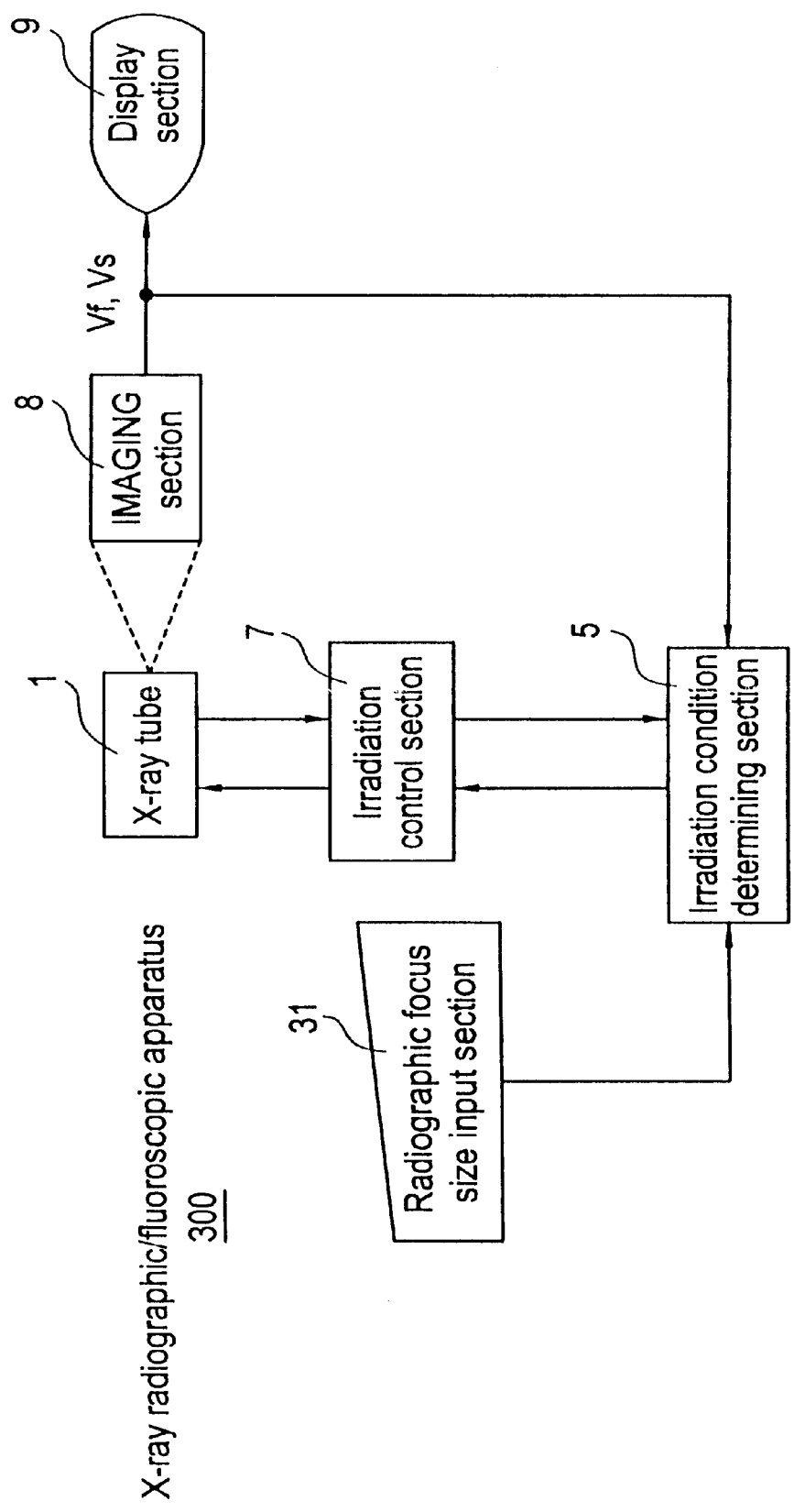
FIG. 8 illustrates the configuration of an X-ray radiographic/fluoroscopic apparatus in accordance with a third embodiment of the present invention.

FIG. 8 illustrates the configuration of an X-ray radiographic/fluoroscopic apparatus in accordance with a third embodiment of the present invention.

The X-ray radiographic/fluoroscopic apparatus 300 comprises a radiographic focus size input section 31 for receiving a radiographic focus size from the operator, and an irradiation condition determining section 5 for determining fluoroscopic irradiation conditions and radiographic irradiation conditions (such as the tube voltage, tube current, exposure dose and radiographic irradiation time Ts). The X-ray tube 1, irradiation control section 7, imaging section 8 and display section 9 are the same components as those of the X-ray radiographic/fluoroscopic apparatus 100 of the first embodiment.

Figure 9:
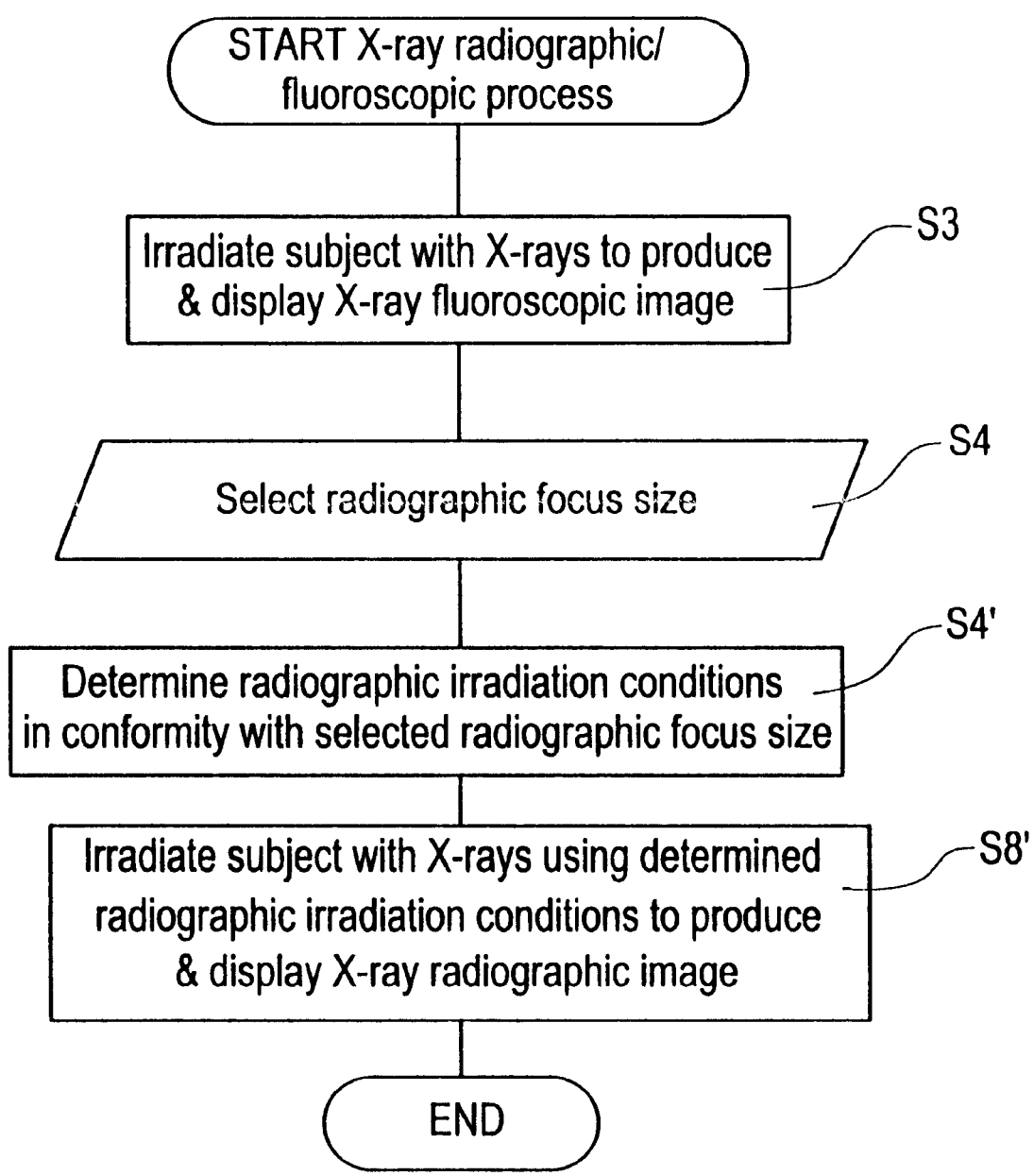
FIG. 9 is a flow chart of an X-ray radiographic/fluoroscopic process by the X-ray radiographic/fluoroscopic apparatus of FIG. 8.

FIG. 9 is a flow chart illustrating an X-ray radiographic/fluoroscopic process by the X-ray radiographic/fluoroscopic apparatus 300.

In Step S3, the subject is irradiated with X-rays based on predefined fluoroscopic irradiation conditions, and an X-ray fluoroscopic image is produced and displayed.

In Step SS4, the operator selects a radiographic focus size using the radiographic focus size input section 31 while viewing the X-ray fluoroscopic image. The selection criterion is any one of (1)–(3) as follows:

(1) If the body thickness of the examined site is relatively large, a large radiographic focus size is selected; and if the body thickness of the examined site is relatively small, a small radiographic focus size is selected.

(2) If the motion of the examined site is relatively large, a large radiographic focus size is selected; and if the motion of the examined site is relatively small, a small radiographic focus size is selected.

(3) A radiographic focus size is previously defined for each examined site. For example, a large radiographic focus size is set for the "Stomach", and a small radiographic focus size is set for the "Small & large intestines".

In Step S4', radiographic irradiation conditions are determined in conformity with the selected radiographic focus size.

In Step S8', the subject is irradiated with X-rays using the determined radiographic irradiation conditions, and an X-ray radiographic image is produced and displayed.

According to the X-ray radiographic/fluoroscopic apparatus 300, since the radiographic focus size is input by the operator, the configuration can be further simplified. Moreover, the operator can finely select a radiographic focus size in conformity with image quality preferences or clinical interest while viewing an X-ray fluoroscopic image.

In addition, the configuration of the above embodiments may be changed as follows:

(1) The fluoroscopic focus size for use in fluoroscopy may be selected from among a plurality of fluoroscopic focus sizes. For example, the fluoroscopic focus size is selected as either of 0.3 mm, 0.6 mm or 1.0 mm according to the examined site. In this case, image quality of the X-ray fluoroscopic image can be improved.

(2) The radiographic focus size for use in radiography may be selected from among three or more radiographic focus sizes. For example, if {radiographic irradiation time Ts—radiographic irradiation time threshold Th}>a, a radiographic focus size of 1.25 mm is selected, if $-b \leq${radiographic irradiation time Ts—radiographic irradiation time threshold Th}≦b, a radiographic focus size of 1.0 mm is selected, and if {radiographic irradiation time Ts—radiographic irradiation time threshold Th}<−b, a radiographic focus size of 0.6 mm is selected. Thus, a radiographic focus size suitable for the examined site can be more finely selected.

(3) If X-ray radiography is performed without X-ray fluoroscopy, the present invention can be applied by selecting a radiographic focus size depending on the examined site (or on the result of estimation of the body thickness or motion in the examined site).

Many widely different embodiments of the invention may be configured without departing from the spirit and the scope of the present invention. It should be understood that the present invention is not limited to the specific embodiments described in the specification, except as defined in the appended claims.

What is claimed is:

1. An X-ray radiographic/fluoroscopic apparatus comprising:

emitting means for emitting X-rays having a focus size that is selectable between at least one fluoroscopic focus size and a plurality of radiographic focus sizes;

fluoroscopic image producing means for producing an X-ray image by irradiating a subject with X-rays having a selected fluoroscopic focus size;

selecting means for selecting a relatively large radiographic focus size in radiographing an examined site having a relatively large body thickness or motion, and for selecting a relatively small radiographic focus size in radiographing an examined site having a relatively small body thickness or motion; and radiographic image producing means for producing an X-ray radiographic image by irradiating said subject with X-rays equivalent to radiographic irradiation conditions determined on basis of said X-ray fluoroscopic image having said selected radiographic focus size.

2. The apparatus of claim 1, wherein said emitting means comprises a plurality of fluoroscopic focus sizes.

3. The apparatus of claim 1, wherein said emitting means comprises three or more radiographic focus sizes.

4. An X-ray radiographic/fluoroscopic apparatus comprising:

emitting means for emitting X-rays having a focus size that is selectable between at least one fluoroscopic focus size and a plurality of radiographic focus sizes;

input means for receiving an examined site from an operator;

threshold defining means for defining a radiographic irradiation time threshold that is an upper limit of a radiographic irradiation time corresponding to said examined site;

fluoroscopic image producing means for producing an X-ray fluoroscopic image by irradiating a subject with X-rays having a selected fluoroscopic focus size;

selecting means for selecting a relatively large radiographic focus size when a radiographic irradiation time determined on basis of said X-ray fluoroscopic image is longer than said time threshold and for selecting a relatively small radiographic focus size when said determined radiographic irradiation time is shorter than said time threshold; and radiographic image producing means for producing an X-ray radiographic image by irradiating said subject with X-rays having a selected radiographic focus size.

5. The apparatus of claim 4, wherein said input means receives from said operator a time threshold which is said upper limit of radiographic irradiation time corresponding to said examined site; and wherein said radiographic image producing means produces said X-ray radiographic image by subjecting said subject to X-rays equivalent to radiographic irradiation conditions determined based on said X-ray fluoroscopic image having said selected radiographic focus size.

6. The apparatus of claim 4, wherein said emitting means comprises a plurality of fluoroscopic focus sizes.

7. The apparatus of claim 4, wherein said emitting means comprises three or more radiographic focus sizes.

8. An X-ray radiographic/fluoroscopic apparatus comprising:

emitting means for emitting X-rays having a focus size that is selectable between at least one fluoroscopic focus size and a plurality of radiographic focus sizes;

input means for receiving an examined site from an operator;

fluoroscopic image producing means for producing an X-ray fluoroscopic image by irradiating a subject with X-rays having a selected fluoroscopic focus size;

determining means for determining radiographic irradiation conditions based on said X-ray fluoroscopic image;

selecting means for selecting a radiographic focus size for use in X-ray radiography based on said examined site and said radiographic irradiation conditions; and radiographic image producing means for producing an X-ray radiographic image by irradiating said subject with X-rays equivalent to said radiographic irradiation conditions and having said selected radiographic focus size.

9. The apparatus of claim 8, wherein said emitting means comprises a plurality of fluoroscopic focus sizes.

10. The apparatus of claim 8, wherein said emitting means comprises three or more radiographic focus sizes.

11. An X-ray radiographic method comprising the steps of:

irradiating a subject with X-rays having a relatively large radiographic focus size in radiographing an examined site having a relatively large body thickness or motion; and irradiating said subject with X-rays having a relatively small radiographic focus size in radiographing an examined site having a relatively small body thickness or motion, thereby to produce an X-ray radiographic image.

12. The method of claim 11, wherein said radiographic focus size for use in said radiography is selected from a group consisting of three or more radiographic focus sizes.

13. An X-ray radiographic/fluoroscopic method comprising the steps of:

producing an X-ray fluoroscopic image by irradiating a subject with X-rays having a fluoroscopic focus size;

determining radiographic conditions based on said X-ray fluoroscopic image;

selecting a radiographic focus size for use in X-ray radiography from a group consisting of a plurality of radiographic focus sizes based on an examined site and said radiographic conditions; and producing an X-ray radiographic image by irradiating said subject with X-rays equivalent to said radiographic conditions and having said selected radiographic focus size.

14. The method of claim 13, wherein said radiographic focus size is selected from a group consisting of three or more radiographic focus sizes.

15. The method of claim 13, comprising the further step of receiving from an operator a radiographic irradiation time threshold that is an upper limit of radiographic irradiation time corresponding to said examined site; and wherein said selecting is of a relatively large radiographic focus size when a radiographic irradiation time determined based on said X-ray fluoroscopic image is longer than said time threshold, and said selecting furthermore is of a relatively small radiographic focus size when said determined radiographic irradiation time is shorter than said time threshold; and wherein said image is produced by irradiating said subject with X-rays equivalent to radiographic irradiation conditions based on said X-ray fluoroscopic image with said selected radiographic focus size.

\* \* \* \* \*